US00PP22575P2

(12) United States Plant Patent
Higaki

(10) Patent No.: US PP22,575 P2
(45) Date of Patent: Mar. 13, 2012

(54) ***HYDRANGEA* PLANT NAMED 'GALILEE'**

(50) Latin Name: ***Hydrangea macrophylla* (Thunb.)**
Varietal Denomination: Galilee

(75) Inventor: Harrison M. Higaki, San Mateo, CA (US)

(73) Assignee: Bay City Flower Company, Half Moon Bay, CA (US)

( * ) Notice: Subject to any disclaimer, the term of this patent is extended or adjusted under 35 U.S.C. 154(b) by 0 days.

(21) Appl. No.: 12/806,808

(22) Filed: Aug. 19, 2010

(51) Int. Cl.
*A01H 5/00* (2006.01)

(52) U.S. Cl. ..... Plt./250

(58) Field of Classification Search ..... Plt./250
See application file for complete search history.

*Primary Examiner* — Annette Para
(74) *Attorney, Agent, or Firm* — James R. Cypher; Charles R. Cypher

(57) ABSTRACT

A new and distinct cultivar of *Hydrangea macrophylla* (Thunb.) named 'Galilee' originated as a controlled cross between *Hydrangea macrophylla* (Thunb.) True Blue - U.S. Plant Pat. No. 18,593 (the seed parent), and the unpatented commercial variety *Hydrangea macrophylla* (Thunb.) 'Mathilda Gutges' (the pollen parent). The cultivar 'Galilee' can be blue or pink depending on the acidity of the soil. The new cultivar is characterized by its sturdy growth habit and its ability to produce blue pigmentation with relatively low levels of soil amendments. The new cultivar has showy inflorescences with large florets.

5 Drawing Sheets

Botanical classification: *Hydrangea macrophylla* (Thunb.) 'Galilee'.

Variety denomination: 'Galilee'.

BACKGROUND OF THE INVENTION

This invention relates to a new and distinct cultivar of the Saxifragaceae family. The botanical name of the plant is *Hydrangea macrophylla* (Thunb.) 'Galilee'.

The new cultivar originated as a seedling from a controlled cross between *Hydrangea macrophylla* (Thunb.) True Blue - U.S. Plant Pat. No. 18,593 (the seed parent), and the unpatented commercial variety *Hydrangea macrophylla* (Thunb.) 'Mathilda Gutges' (the pollen parent).

The variety 'Galilee' has stronger stems than 'Mathilda Gutges' and larger florets than either 'True Blue' or 'Mathilda Gutges'. The sepals of the new variety develop a deeper blue tone with the addition of less aluminum than its parent 'True Blue'.

TABLE 1

| | New Variety 'Galilee' | U.S. Plant Pat. No. 18,593 'True Blue' | Unpatented 'Mathilda Gutges' |
|---|---|---|---|
| Stem strength | Strong | Strong | Strong |
| Pigmentation of Sepals | R.H.S. 100B (blue group) Easier to produce a more blue pigmentation with less alumina than parents | R.H.S 100D (blue group) | R.H.S. 83C (violet group) at edges of sepals. R.H.S. 98A (violet-blue group) in center of sepals. |
| Sepal margins | Dentate | Dentate | Serrate |
| Floret Size | Larger than Parents | Smaller than 'Galilee' | Smaller than 'Galilee' |

Asexual reproduction was first accomplished when vegetative cuttings were taken from the initially selected plant. Examination of asexually reproduced, successive generations grown at a nursery at Half Moon Bay, Calif., under the direction of the inventor show that the combination of characteristics as herein disclosed for 'Galilee' remains firmly fixed through three generations.

DESCRIPTION OF THE DRAWINGS

The accompanying drawings consist of color photographs that show the typical plant form, including the inflorescence, foliage, and sepals.

DESCRIPTION OF THE NEW PLANT

Figure 1:
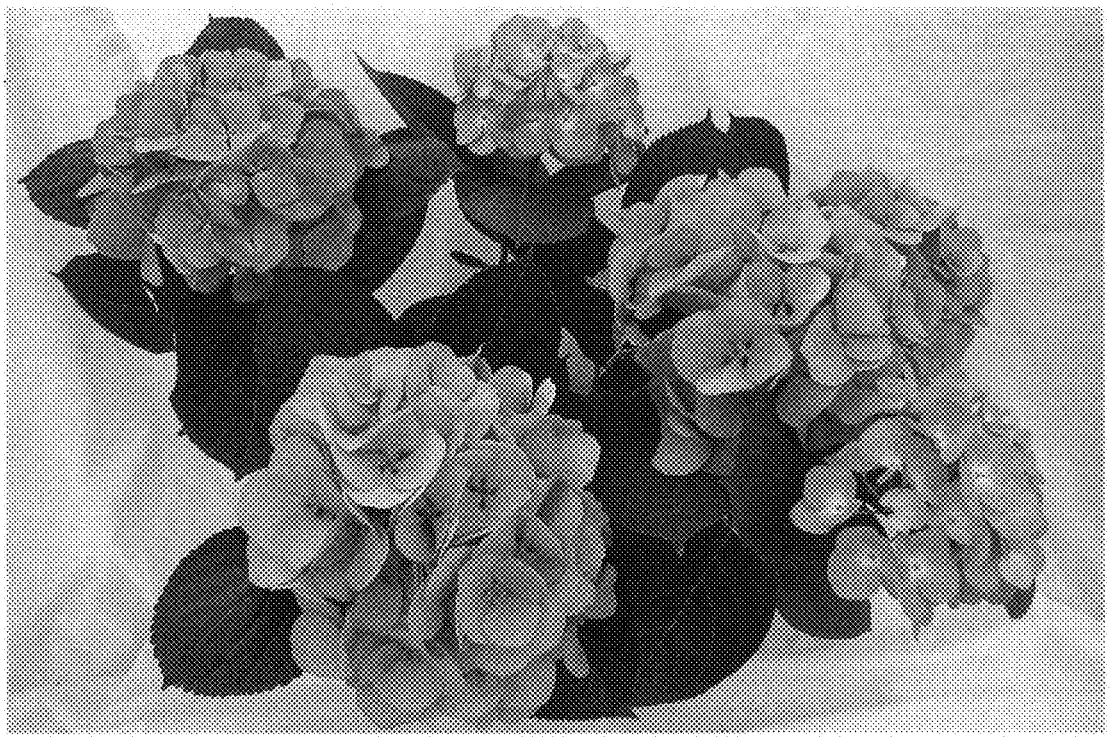
FIG. 1 is a top view of the entire plant, showing its form, compact growth habit, dark green foliage, and its inflorescence.
Figure 2:
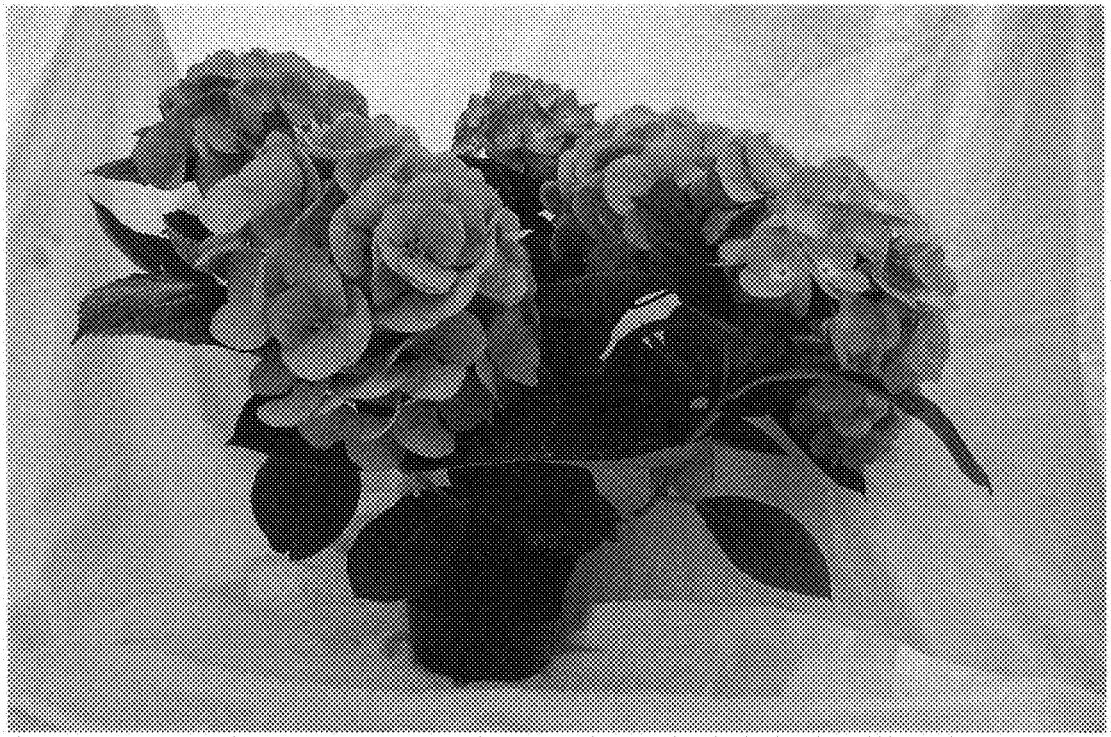
FIG. 2 is a side view of the entire plant.
Figure 3:
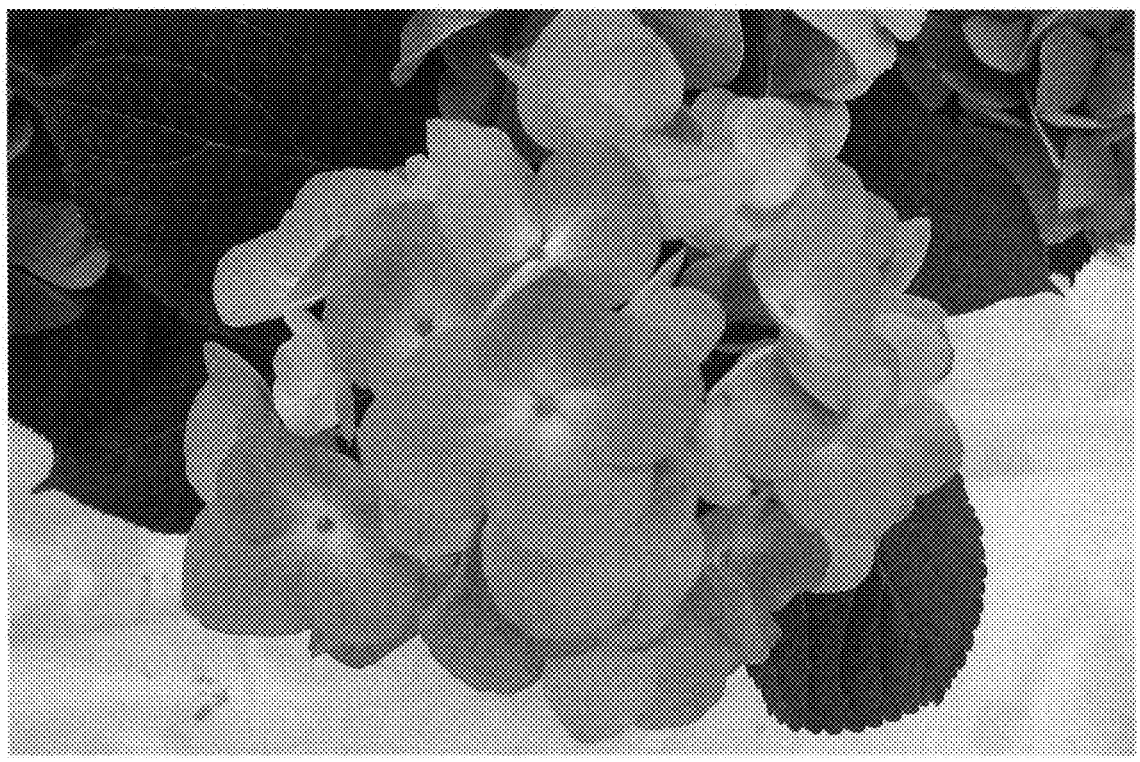
FIG. 3 is a close-up view of a panicle of the new variety. The panicle shown is immature.
Figure 4:
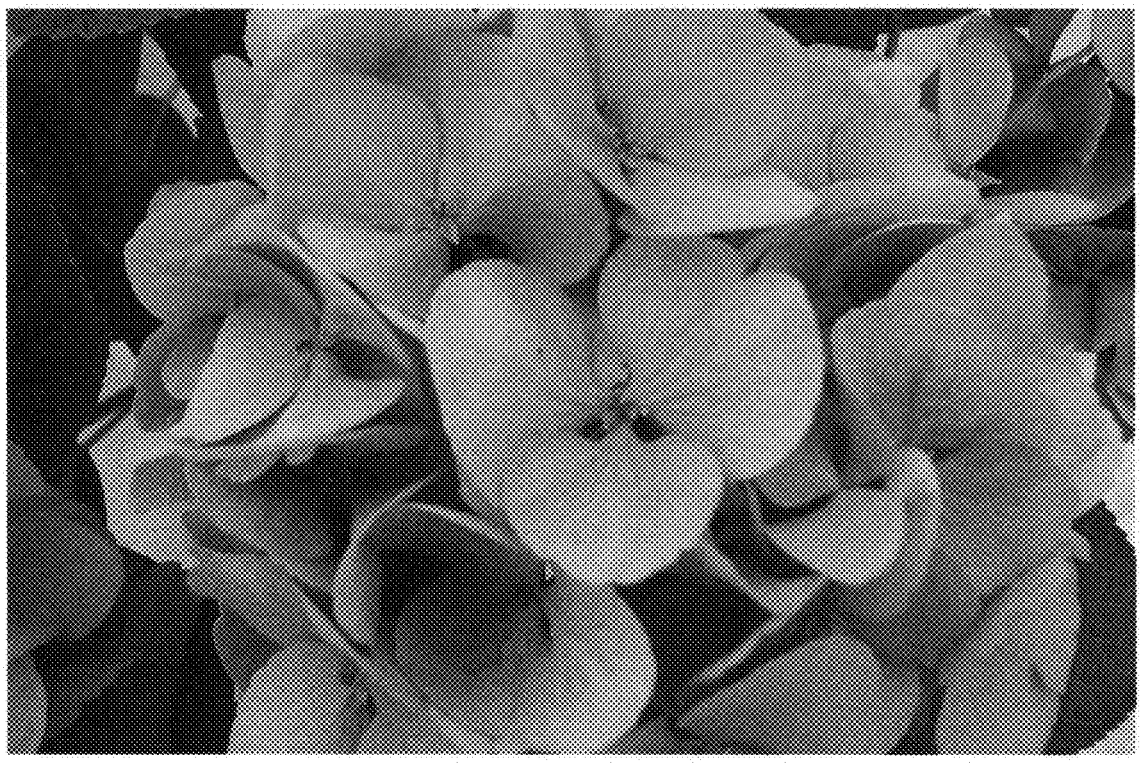
FIG. 4 is a close-up view of a panicle of the new variety. The panicle shown is mature.
Figure 5:
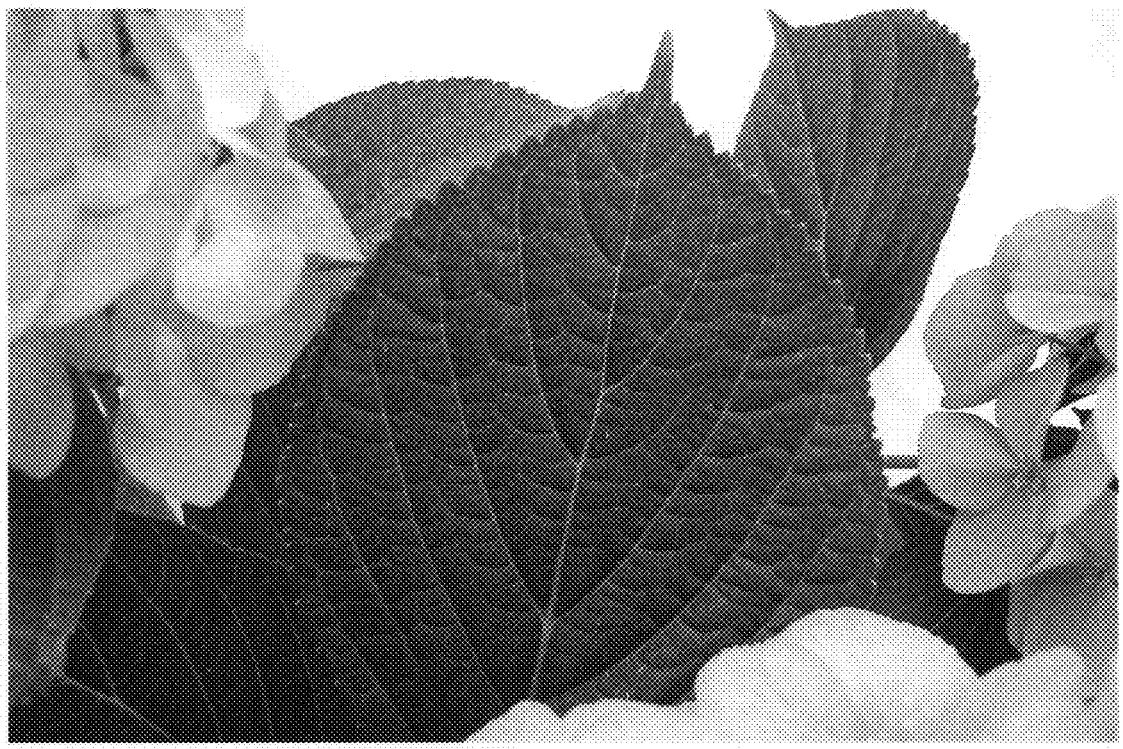
FIG. 5 is a close-up view of the adaxial surface of a mature leaf.
Figure 6:
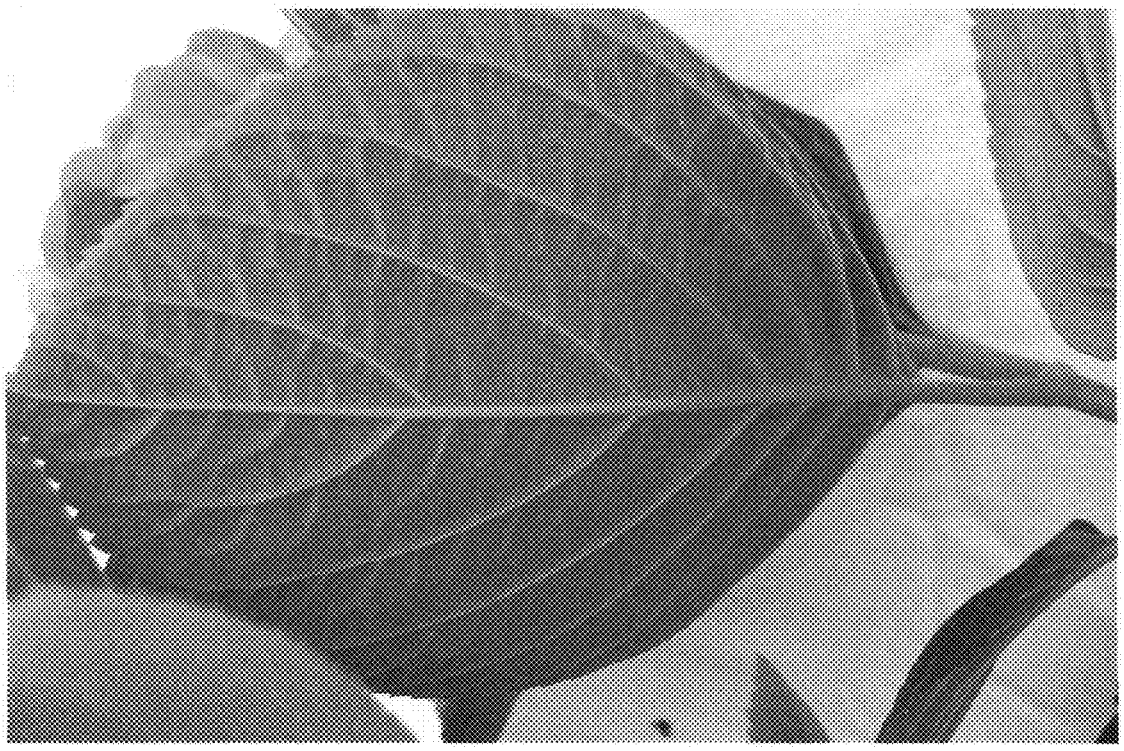
FIG. 6 is a close-up view of the abaxial surface of a mature leaf.
Figure 7:
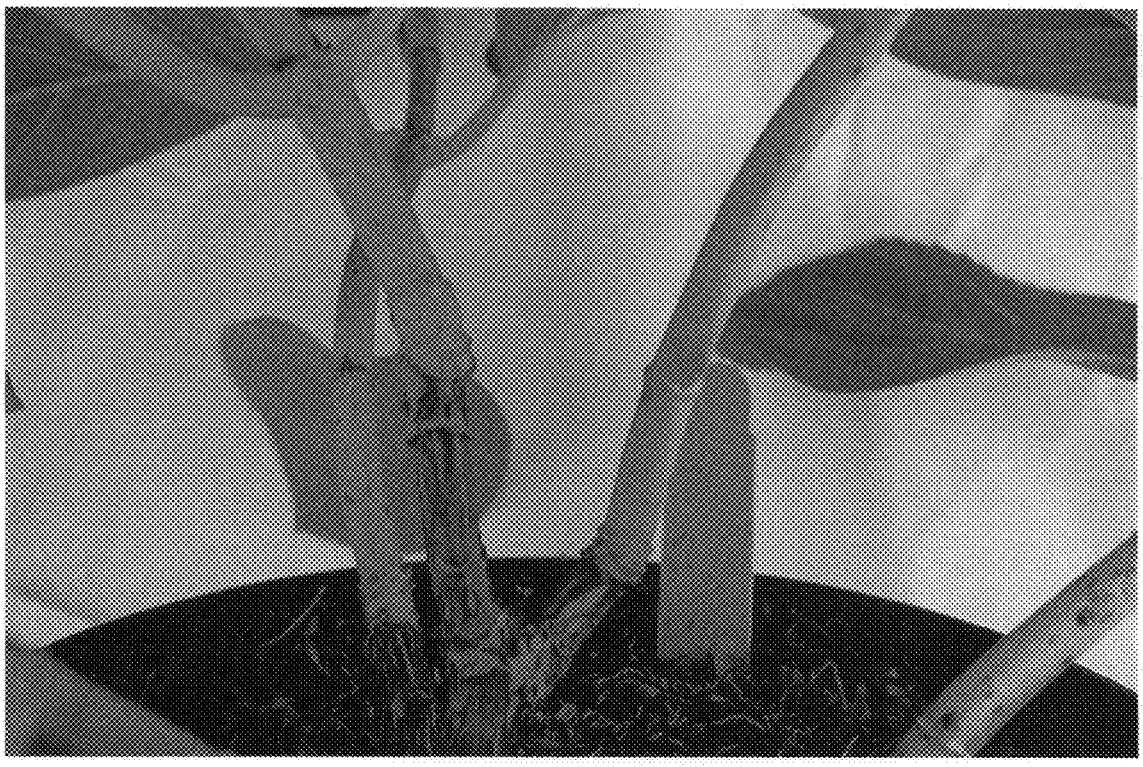
FIG. 7 is a close-up view of the base of the stem.
Figure 8:
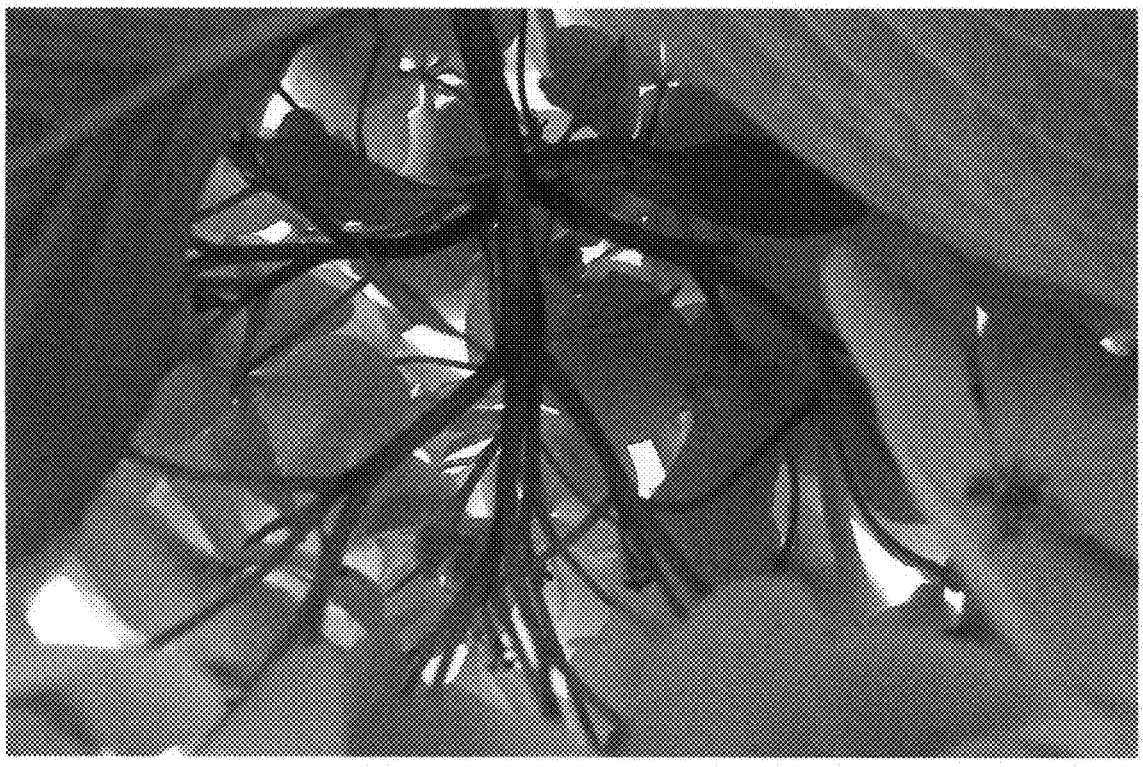
FIG. 8 is a close-up view of the underside of a panicle of the new variety.
Figure 9:
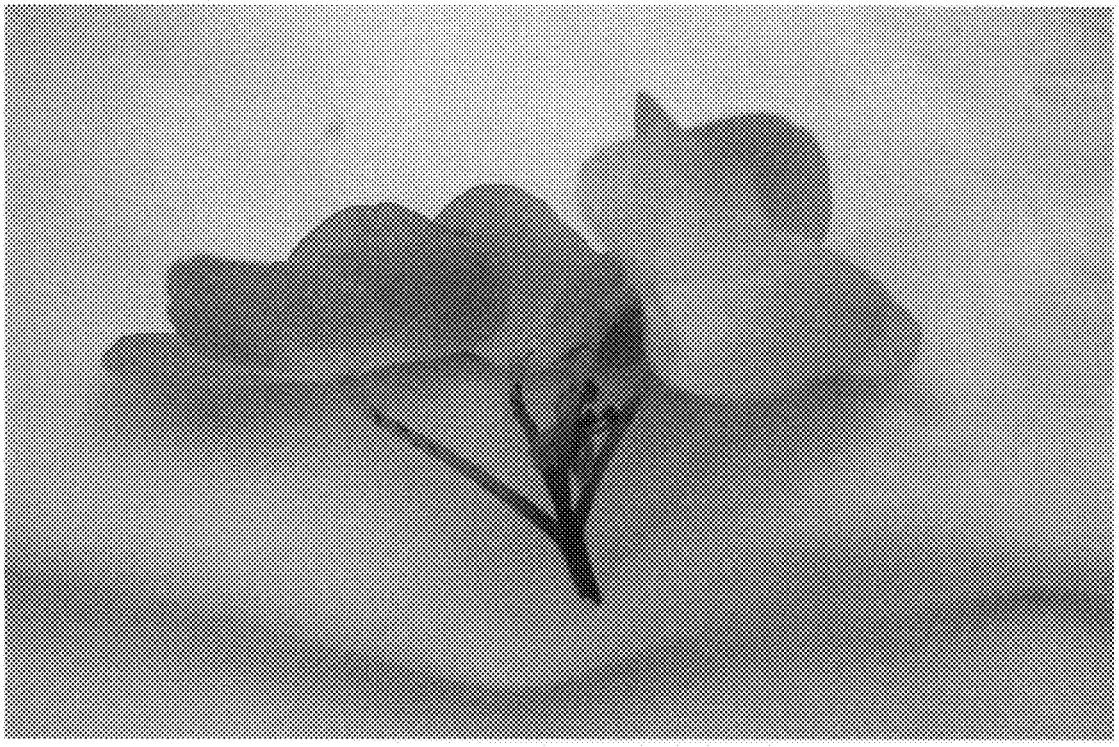
FIG. 9 is a close-up view of a cyme of the new variety, showing sepalous florets and a non-sepalous floret.

The plants shown in the figures are ready for commercial sale and started out as cuttings, taken from the stem of a grown plant.

'Galilee' has not been observed under all possible environmental conditions. The phenotype may vary significantly with variations in environment such as temperature, light intensity and day length. Color determinations were made with The Royal Horticultural Society (R.H.S.) Colour Chart.

THE PLANT

Origin: Controlled cross between *Hydrangea macrophylla* (Thunb.) True Blue - U.S. Plant Pat. No. 18,593 (the seed parent), and the unpatented commercial variety *Hydrangea macrophylla* (Thunb.) 'Mathilda Gutges' (the pollen parent).

Form: Upright, compact shrub. A typical plant with a mature inflorescence that is ready for sale is approximately 17" high and has a diameter of 18" when grown in a 6" pot with appropriate soil amendments.

Growth: Upright, vigorous growth habit. Inflorescence is large. The plant branches easily when pinched with shoots forming at the base of the plant. Lateral branches are similar in appearance and form to the main stems.

Stems: Lenticels are present, generally they are 1 to 2 mm long. Lenticel color is R.H.S. 86A (violet group). Young stems are smooth. Stems become woody as they age. Stems are 5 to 7 mm in diameter. The color of typical young stems and young lateral branches is R.H.S. 144 B (yellow-green group). Older, woody stems are R.H.S. 197 A (greyed-green group).

Foliage: Abundant. Leaves are opposite on stem and lateral branches.

*Shape of leaf.*—Elliptic with acute base and apex. Margins are serrate.

*Texture.*—Glabrous; veins dominate on the underside of the leaf and are sunken on the leaf surface.

*Color.*—Mature leaves have an adaxial side that is R.H.S. 147 A (yellow-green group), and an abaxial side that is R.H.S. 138 B (green group). Leaves are pinnately veined. The midvein and veins branching off the midvein are large and prominent on the underside of the leaves. Leaves are as wide as 13.5 cm and 21 cm long. Petioles are typically 2.5 cm long and 4 mm wide. Petioles are R.H.S. 138 B (green group).

BUDS

Form: Globose with 4 to 5 connate petals. Buds in the center of the inflorescence are non-sepalous. Buds are approximately 1 mm by 1 mm when very young. Buds can be 4 mm in diameter and still unopened. Petals of mature buds are R.H.S. 100B (blue group).

Aspect: Smooth.

Arrangement: Borne on branched panicles.

INFLORESCENCE

Form: Paniculate. Terminal. As many as 100 or more individual flowers (florets) per inflorescence. Both sepalous florets and non-sepalous florets borne on same panicle, although there are very few non-sepalous florets, just the first florets on individual cymes. Flowers do not produce a fragrance. The peduncle or panicle for the inflorescence is strong and upright. Sepalous florets have anthers and style.

Size of inflorescence: Individual inflorescence size is dependent on the number of florets. A typical inflorescence can grow as large as large as 6" in diameter, and 4.5" high.

Shape: Globose. Clusters of numerous small florets; sepalous florets are flat and overlapping one another. Sepals are persistent.

Appearance: Showy.

FLORETS

*General.*—The non-sepalous florets at the center of the cymes open first. Sepalous florets are perfect and complete. Corolla: Generally the petals fall off as flower matures. Petals are typically 4 mm long and 3 mm wide. Pedicels are of variable length depending on the age of the floret. Pedicels to un-opened, non-sepalous florets are generally 4 mm and length. Pedicels to mature, opened sepaolus florets can be as long as 40 mm. Lenticels are present on pedicels-1 mm in length. Color of lenticels farther away from floret is R.H.S. 86A (violet group). Color of the pedicel is variable along the length of the floret. The color of the pedicel closer to the floret is R.H.S. 145C (yellow-green group) with the transition area closest to the floret being R.H.S. 100B (blue group).

*Stamens.*—8-10 stamens (mostly 10). Pollen is white-R.H.S. 158C (yellow-white group). Plant produces abundant pollen. Filament is approximately 3 mm long. Filament is R.H.S. 100B (blue group). Anther is 1 mm long and is regular and basally attached.

*Pistil.*—Two to three style each floret, although most florets have two style. Each style has one stigma. Style is typically 2 mm long. Sytle is R.H.S. 100B (blue group). Stigma is R.H.S. 95 A (violet-blue group).

*Ovary.*—Ovary is partially inferior.

Sepalous florets:

*General.*—Veins dominate on the underside of the sepals. Sepalous florets are complete.

*Number of sepals.*—3 or 4 sepals per floret, usually 4.

*Aspect of sepals.*—Smooth and glaucescent.

*Shape of sepals.*—Reniform with acuminate apex. Edges are dentate, often wavy when the floret is young.

*Size of sepals.*—As the florets mature, the sepals enlarge and overlap each other more and more, until, often, there is no space between the sepals when the petals of the florets open. Sepals at maturity are typically 35 mm long and 40 mm wide. Flowers are typically 60 mm in diameter. Sepals are R.H.S. 100 B (blue group) at maturity. Sepal pigmentation develops at the tips and spreads to base of sepals which is R.H.S. 155A (white group).

Fruit: None.

Fragrance: None.

I claim:

1. A new and distinct *Hydrangea macrophylla* plant named 'Galilee' substantially as herein shown and described.

* * * * *